United States Patent [19]

Petitpierre

[11] 4,083,866
[45] Apr. 11, 1978

[54] SULFONYLAMIDINO AMINOBENZALDEHYDE COMPOUNDS

[75] Inventor: Jean Claude Petitpierre, Kaiseraugst, Switzerland

[73] Assignee: Ciba-Geigy Corporation, Ardsley, N.Y.

[21] Appl. No.: 737,770

[22] Filed: Nov. 1, 1976

[30] Foreign Application Priority Data

Nov. 24, 1975 Switzerland .................. 15199/75

[51] Int. Cl.$^2$ ........................................... C07C 143/80
[52] U.S. Cl. ......................... 260/556 B; 260/326.82; 260/293.73; 260/392; 260/394; 260/556 C; 542/416
[58] Field of Search ............... 260/556 B, 556 C, 392, 260/394

[56] References Cited

U.S. PATENT DOCUMENTS

| 2,312,404 | 3/1943 | Haack | 260/556 B X |
|---|---|---|---|
| 3,325,541 | 6/1967 | Aumuller | 260/556 C |
| 3,377,357 | 4/1968 | Traverso | 260/556 C X |
| 3,455,939 | 7/1969 | Loev et al. | 260/556 C X |
| 3,819,603 | 6/1974 | Shen et al. | 260/240 G X |
| 3,953,492 | 4/1976 | Mrozik | 260/556 B X |
| 3,953,493 | 4/1976 | Vanden Heuvel | 260/556 B X |

FOREIGN PATENT DOCUMENTS 538,822  8/1941  United Kingdom.

Primary Examiner—Daniel E. Wyman
Assistant Examiner—Thomas A. Waltz
Attorney, Agent, or Firm—Edward McC. Roberts; Michael W. Glynn; Prabodh I. Almaula

[57] ABSTRACT

Aminobenzaldehyde compounds which correspond to the general formula

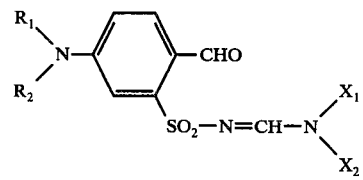

wherein
$R_1$, $R_2$, $X_1$ and $X_2$ independently of one another represent alkyl having 1 to 12 carbon atoms, alkoxyalkyl having 2 to 8 carbon atoms, cycloalkyl having 5 or 6 carbon atoms, or optionally substituted benzyl or phenyl, and
$X_1$ and $X_2$ can also represent hydrogen, or
the substituent pairs $R_1$ and $R_2$ and $X_1$ and $X_2$ independently of one another each represent together with the nitrogen atom linking them a 5- or 6-membered heterocyclic radical; these compounds are particularly useful as intermediate products for the manufacture of color formers.

9 Claims, No Drawings

SULFONYLAMIDINO AMINOBENZALDEHYDE COMPOUNDS

The present invention relates to substituted aminobenzaldehyde compounds and to processes for producing them.

The novel compounds correspond to the general formula:

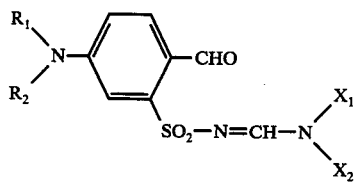

wherein $R_1$, $R_2$, $X_1$ and $X_2$ independently of one another represent alkyl having 1 to 12 carbon atoms, alkoxyalkyl having 2 to 8 carbon atoms, cycloalkyl having 5 or 6 carbon atoms, or optionally substituted benzyl or phenyl, and $X_1$ and $X_2$ can also represent hydrogen, or the substituent pairs $R_1$ and $R_2$ and $X_1$ and $X_2$ independently of one another each represent together with the nitrogen atom linking them a 5- or 6-membered, preferably saturated, heterocyclic radical.

If the substituents $R_1$, $R_2$, $X_1$ and $X_2$ represent alkyl groups, they can be straight-chain or branched-chain alkyl groups. Examples of such alkyl groups are methyl, ethyl, n-propyl, isopropyl, n-butyl, sec.-butyl, n-hexyl, n-octyl or n-dodecyl. If the R- or X-substituents represent alkoxyalkyl groups, these can contain 1 to 4 carbon atoms in each of the alkyl moieties. Preferred alkoxyalkyl radicals are β-methoxyethyl or β-ethoxyethyl. Examples of cycloalkyl as R- and X-radicals are cyclopentyl and preferably cyclohexyl. Optionally present substituents in the benzyl or phenyl group are, e.g., alkyl having 1 to 4 carbon atoms, alkoxy having 1 to 4 carbon atoms, alkanoyl having 1 to 4 carbon atoms, nitro or halogens, e.g. fluorine, bromine or particularly chlorine. Examples of these araliphatic or aromatic radicals are p-methylbenzyl, o- or p-chlorobenzyl, o- or p-nitrobenzyl, o- or p-tolyl, xylyl, o-, m- or p-chlorophenyl or o- or p-nitrophenyl.

If the substituent pairs $R_1$ and $R_2$ and $X_1$ and $X_2$ each represent together with the common nitrogen atom a heterocyclic radical, this is, for example, pyrrolidino, piperidino, pipecolino, morpholino, thiomorpholino or piperazino.

Of primary interest are aminobenzaldehyde compounds of the general formula

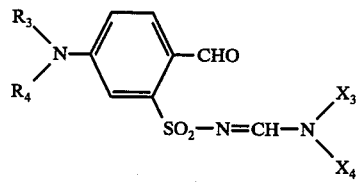

wherein $R_3$ and $R_4$ each represent alkyl having 1 to 4 carbon atoms or benzyl, $X_3$ represents hydrogen, alkyl having 1 to 4 carbon atoms, phenyl, chlorophenyl, nitrophenyl or benzyl, and $X_4$ represents hydrogen or alkyl having 1 to 4 carbon atoms, or the substituent pairs $R_3$ and $R_4$ and $X_3$ and $X_4$ independently of one another represent pyrrolidino or piperidino.

Among these aminobenzaldehyde compounds, those to be emphasized in particular are the compounds wherein $R_3$ and $R_4$ both represent methyl or ethyl, $X_3$ represent hydrogen, methyl, ethyl, phenyl, p-chlorophenyl or p-nitrophenyl, and $X_4$ represents hydrogen, methyl or ethyl, or $X_3$ and $X_4$ together with the common nitrogen atom represent pyrrolidino or piperidino. Compounds of formula (2) which are even more preferred are those wherein $R_3$ and $R_4$ both represent methyl or ethyl, $X_3$ represents methyl, ethyl or phenyl, and $X_4$ represents hydrogen, methyl or ethyl; and especially those compounds of formula (2) wherein $X_3$ and $X_4$ both represent methyl or ethyl.

The novel compound of the general formula (1) are obtained by reacting a metanilic acid amide of the general formula

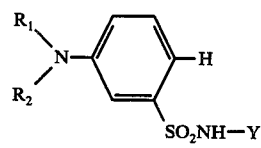

wherein $R_1$ and $R_2$ have the aforementioned meaning, and

Y represents hydrogen, alkyl having 1 to 4 carbon atoms or alkanoyl having 1 to 4 carbon atoms, with a formamide of the general formula

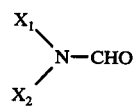

wherein $X_1$ and $X_2$ have the given meaning, in the presence of an acid halide.

Acid halides which can be used are acid bromides or preferably acid chlorides of phosphorous or sulphurous acid, of phosphoric acid, of sulphuric acid, of carbonic acid or oxalic acid. Those advantageously used are oxalyl chloride, oxalyl bromide, thionyl chloride, sulphuryl chloride, phosphorous trichloride, phosphorus tribromide or preferably phosgene or in particular phosphorous oxychloride.

The reaction of the metanilic acid of formula (3) with the formamide of formula (4) can be performed at a temperature of between $-10°$ and $+120°$ C, preferably between 20° and 100° C. It is advantageous to maintain anhydrous conditions. An excess of formamide or of the acid halide can be used as the reaction medium; however, it is also possible, especially in the case of gaseous acid halides, to use a solvent which is inert under the reaction conditions.

Suitable solvents are, for example: cycloaliphatic or aromatic hydrocarbons such as cyclohexane, benzene, toluene or xylene; chlorinated hydrocarbons such as chloroform or carbon tetrachloride; ethers such as dioxane, diethyl ether, glycol dimethyl ether or tetrahydrofuran.

The concentration of the reactants is not critical; it is of advantage, however, to use at least two molar equivalents of the formylating agent of formula (4). The production process is performed as a rule by firstly reacting the formylating agent of formula (4) with the acid halide, and then adding the compound of formula (3). It is however also possible to bring together all the reactants simultaneously, i.e. the compound of formula (3), the compound of formula (4) and the acid halide. The isolation of the final product of formula (1) is performed in the generally known manner, e.g. by pouring the reaction mixture into ice water, optionally with neutralising of the mineral acids with an alkaline compound, e.g. alkali metal hydroxides or alkali metal carbonates; filtering off the formed precipitate, washing and drying; as well as optionally by recrystallising the product. Liquid final products can be obtained by extraction with suitable organic solvents, and optionally purified by distillation.

The metanilic acid amides of formula (3) are for the most part known. Preferred compounds of formula (3) are those wherein Y represents hydrogen. On reaction of the compounds of formula (3) with the formylating agents of formula (4) there occurs not only the introduction of a formyl group into the benzene nucleus of the aniline compound, but also the formation simultaneously of an —N=CH group with the amide nitrogen. If Y in the starting materials of formula (3) represents an alkyl or alkanoyl group, the formation of azomethine occurs with simultaneous splitting-off of the alkyl or acyl group Y.

The following may be mentioned as examples of metanilic acid amides used as starting materials of formula (3):

$N^3,N^3$-dimethyl-metanilic acid amide,
$N^3,N^3$-diethyl-metanilic acid amide,
$N^3,N^3$-dipropyl-metanilic acid amide,
$N^3,N^3$-dimethyl-metanilic acid-$N^1$-methylamide,
$N^3,N^3$-dimethyl-metanilic acid-$N^1$-ethylamide,
$N^3,N^3$-dimethyl-metanilic acid-$N^1$-acetylamide,
$N^3,N^3$-diethyl-metanilic acid-$N^1$-methylamide,
$N^3,N^3$-diethyl-metanilic acid-$N^1$-ethylamide,
$N^3,N^3$-diethyl-metanilic acid-$N^1$-acetylamide,
$N^3,N^3$-dibenzyl-metanilic acid amide.

Preferred formylating agents are those which correspond to the final materials of formula (2). The following are for example suitable: formamide, dimethylformamide, diethylformamide, N-formyl-N-methylaniline, N-ethyl-N-formylaniline, 4-chloro-N-formyl-N-methylaniline, 4-nitro-N-formyl-N-methylaniline, N-formyl-cyclohexylamine, N-formylpyrrolidine and N-formyl-piperidine. Dimethylformamide and diethylformamide have however proved to be the most suitable among these.

The novel compounds of the general formulae (1) and (2) are valuable intermediates for the production of dyes, pigments, optical brighteners, plant protective agents and pharmaceutical preparations. They can be used in particular as starting materials for producing colour formers, e.g. of the triarylmethane series; or colour formers which undergo a bond splitting as a result of protonisation or reaction with a Lewis acid.

In the following Examples, percentages are expressed as percent by weight.

EXAMPLE 1

18 ml of phosphorous oxychloride is added dropwise at 0° – 5° C to 36 ml of dimethylformamide. The mixture is stirred for 2 hours at room temperature, and then 13.7 g of $N^3,N^3$-diethyl-metanilic acid amide is added. The reaction mixture is heated to 70° – 75° C and stirred for 48 hours at this temperature. It is thereupon treated with ice and the pH value is adjusted to 2.5 with 40% sodium hydroxide solution. The formed precipitate is filtered off and washed neutral with water. After drying, there is obtained 9.2 g of a compound of the formula

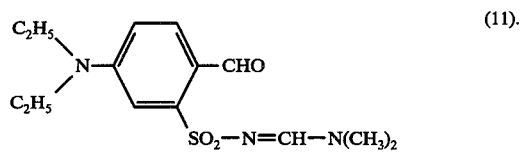

A specimen recrystallised from aqueous methanol has a melting point of 162° – 163° C.

Analysis: $C_{14}H_{21}N_3O_3S$ Calculated: C, 54.00; H, 6.80; N, 13.49; S, 10.30%. Found: C, 53.9; H, 6.7; N, 13.3; S, 10.3%.

EXAMPLE 2

8.2 g of a product which is identical to the compound of formula (11) is obtained by replacing in Example 1 the $N^3,N^3$-diethyl-metanilic acid amide with 16.2 g of $N^1$-acetyl-$N^3,N^3$-diethyl-metanilic acid amide and proceeding otherwise in the manner described in Example 1.

EXAMPLE 3

4.4 g of a product which is identical to the compound of formula (11) is obtained by replacing in Example 1 the $N^3,N^3$-diethyl-metanilic acid amide with 14.6 g of $N^1$-methyl-$N^3,N^3$-diethyl-metanilic acid amide and proceeding otherwise in the manner described in Example 1.

EXAMPLE 4

If the $N^3,N^3$-diethyl-metanilic acid amide in Example 1 is replaced with 12.0 g of $N^3,N^3$-dimethyl-metanilic acid amide, with the procedure otherwise being as described in Example 1, there is obtained 9.5 g of a compound of the formula

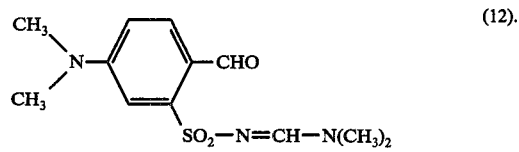

A specimen recrystallised from methanol has a melting point of 183° – 184° C.

Analysis: $C_{12}H_{17}N_3O_3S$

Caculated: C, 50.87; H, 6.05; N, 14.83; S, 11.32%. Found: C, 50.9; H, 6.0; N, 14.7; S, 11.2%.

EXAMPLE 5

13.8 ml of phosphorus oxychloride is added dropwise within 90 minutes at 5°–10° C to 20.3 g of N-formyl-N-methylaniline. The mixture is stirred for 1 hour at 30° C, and then cooled to 5° C. An addition is made at 5°–10°

C of 60 ml of trichloroethane and subsequently of 22.8 g of $N^3$, $N^3$-diethyl-metanilic acid amide, and the mixture is stirred for 60 hours at 80° C. After removal of the solvent by evaporation in vacuo, the residue is processed in the manner described in Example 1. There are obtained 12.2 g of a compound of the formula

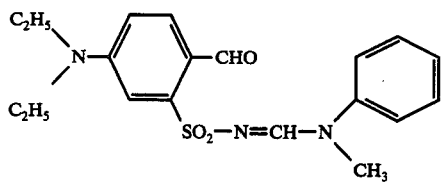

(13).

A specimen recrystallised from a mixture of 5 parts of ethanol and one part of acetone has a melting point of 177°–178° C.

Analysis: $C_{19}H_{23}N_3O_3S$ Calculated: C, 61.10; H, 6.21; N, 11.25; S, 8.59%. Found: C, 60.9; H, 6.3; N, 11.3; S, 8.9%.

I claim:

1. An aminobenzaldehyde compound of the formula

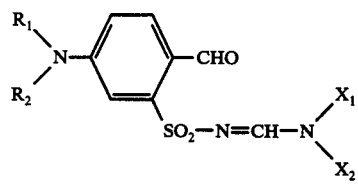

(I)

wherein $R_1$, $R_2$, $X_1$ and $X_2$ independently of one another represent alkyl having 1 to 12 carbon atoms, alkoxyalkyl having 2 to 8 carbon atoms, cycloalkyl having 5 or 6 carbon atoms, phenyl, benzyl or substituted benzyl or phenyl, said substituents being chosen from alkyl, alkoxy, alkanoyl, nitro, and halogens, and $X_1$ and $X_2$ are also hydrogen.

2. A compound according to claim 1 of the formula

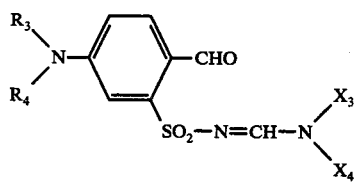

(2)

wherein $R_3$ and $R_4$ each represent alkyl having 1 to 4 carbon atoms or benzyl, $X_3$ represents hydrogen, alkyl having 1 to 4 carbon atoms, phenyl, chlorophenyl, nitrophenyl or benzyl, and $X_4$ represents hydrogen or alkyl having 1 to 4 carbon atoms.

3. A compound according to claim 2, wherein $R_3$ and $R_4$ both represent methyl or ethyl, $X_3$ represents hydrogen, methyl, ethyl, phenyl, p-chlorophenyl or p-nitrophenyl, and $X_4$ represents hydrogen, methyl or ethyl.

4. A compound according to claim 2, wherein $R_3$ and $R_4$ both represent methyl or ethyl, $X_3$ represents methyl, ethyl or phenyl, and $X_4$ represents hydrogen, methyl or ethyl.

5. A compound according to claim 2, wherein $X_3$ and $X_4$ both represent methyl or ethyl.

6. A process for the production of aminobenzaldehyde compounds of the general formula

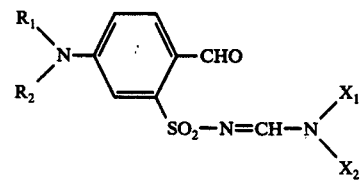

(I)

wherein $R_1$, $R_2$, $X_1$ and $X_2$ independently of one another represent alkyl having 1 to 12 carbon atoms, alkoxyalkyl having 2 to 8 carbon atoms, cycloalkyl having 5 to 6 carbon atoms, benzyl, phenyl or substituted benzyl or phenyl, said substituents being chosen from alkyl, alkoxy, alkanoyl, nitro, and halogens, and $X_1$ and $X_2$ are also represent hydrogen, which process comprises reacting a metanilic acid amide of the general formula

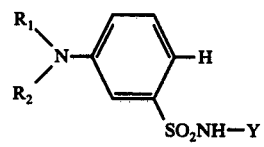

(3)

wherein $R_1$ and $R_2$ have the aforementioned meaning, and Y represents hydrogen, alkyl having 1 to 4 carbon atoms or alkanoyl having 1 to 4 carbon atoms, with a formamide of the general formula

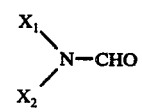

(4), wherein $X_1$ and $X_2$ have the aforementioned meaning, in the presence of an acid halide.

7. A process according to claim 6, wherein there is used a compound of formula (3) wherein Y represents hydrogen.

8. A process according to claim 6, wherein there is used a compound of formula (3) wherein Y is acetyl.

9. A process according to claim 6, wherein there is used a compound of formula (3) wherein Y is methyl or ethyl.

* * * * *